US00PP24512P3

(12) United States Plant Patent
Simpson et al.

(10) Patent No.: US PP24,512 P3
(45) Date of Patent: Jun. 3, 2014

(54) STRAWBERRY PLANT NAMED 'BUDDY'

(50) Latin Name: *Fragaria×ananassa*
Varietal Denomination: Buddy

(75) Inventors: David William Simpson, East Malling (GB); Adam Barrie Whitehouse, Maidstone (GB); Abigail Wendy Johnson, Rochester (GB)

(73) Assignee: Hargreaves Plants Limited, Spalding, Lincolnshire (GB)

( * ) Notice: Subject to any disclaimer, the term of this patent is extended or adjusted under 35 U.S.C. 154(b) by 49 days.

(21) Appl. No.: 13/573,192

(22) Filed: Aug. 29, 2012

(65) Prior Publication Data

US 2013/0097755 P1 Apr. 18, 2013

(51) Int. Cl.
*A01H 5/00* (2006.01)

(52) U.S. Cl.
USPC ..... Plt./209

(58) Field of Classification Search
USPC ..... Plt./209
See application file for complete search history.

*Primary Examiner* — Annette Para
(74) *Attorney, Agent, or Firm* — Jondle Plant Sciences Division of Swanson & Bratschun, L.L.C.

(57) ABSTRACT

A new and distinct variety of strawberry plant named 'Buddy' particularly characterized by an everbearing plant with good vigor, producing attractive, glossy berries with excellent eating quality, is disclosed.

3 Drawing Sheets

Genus and species: *Fragaria×ananassa.*
Variety denomination: 'Buddy'.

CROSS REFERENCE TO RELATED APPLICATIONS

This application claims the benefit of priority from EU Community Plant Variety Rights (CPVR) application no. 20112458, filed Oct. 17, 2011, which is incorporated herein by reference in its entirety.

BACKGROUND OF THE NEW PLANT

The present invention relates to a new and distinct everbearing strawberry variety designated 'Buddy' and botanically known as *Fragaria×ananassa.* This new strawberry variety was discovered as a seedling in East Malling, Kent, United Kingdom in 2006 and originated from a cross made in March 2005 between the female parent 'Diamante' (U.S. Plant Pat. No. 10,435) and the male parent 'DNBL205' (unpatented). 'Buddy' was first fruited at East Malling Reasearch (EMR) in East Malling, Kent in 2006, and originally designated EMR428.

The present invention has been found to retain its distinctive characteristics through successive asexual propagations via stolons.

Plant Breeder's Rights for this variety have been applied for in Europe on Oct. 17, 2011 having CPVR application no. 20112458. 'Buddy' has not been made publicly available or sold anywhere in the world more than one year prior to the filing date of this application.

SUMMARY OF THE INVENTION

The following are the most outstanding and distinguishing characteristics of this new cultivar when grown under normal horticultural practices in East Malling, Kent, United Kingdom.

1. Everbearing plant;
2. Good vigor; and
3. Attractive, glossy berries with excellent eating quality.

DESCRIPTION OF THE PHOTOGRAPHS

The accompanying color photographs show typical specimens of the new variety at various stages of development. The colors shown are as true as can be reasonably obtained by conventional photographic procedures. The photographs were taken from 2.5 month-old plants.

DESCRIPTION OF THE NEW VARIETY

Figure 1:
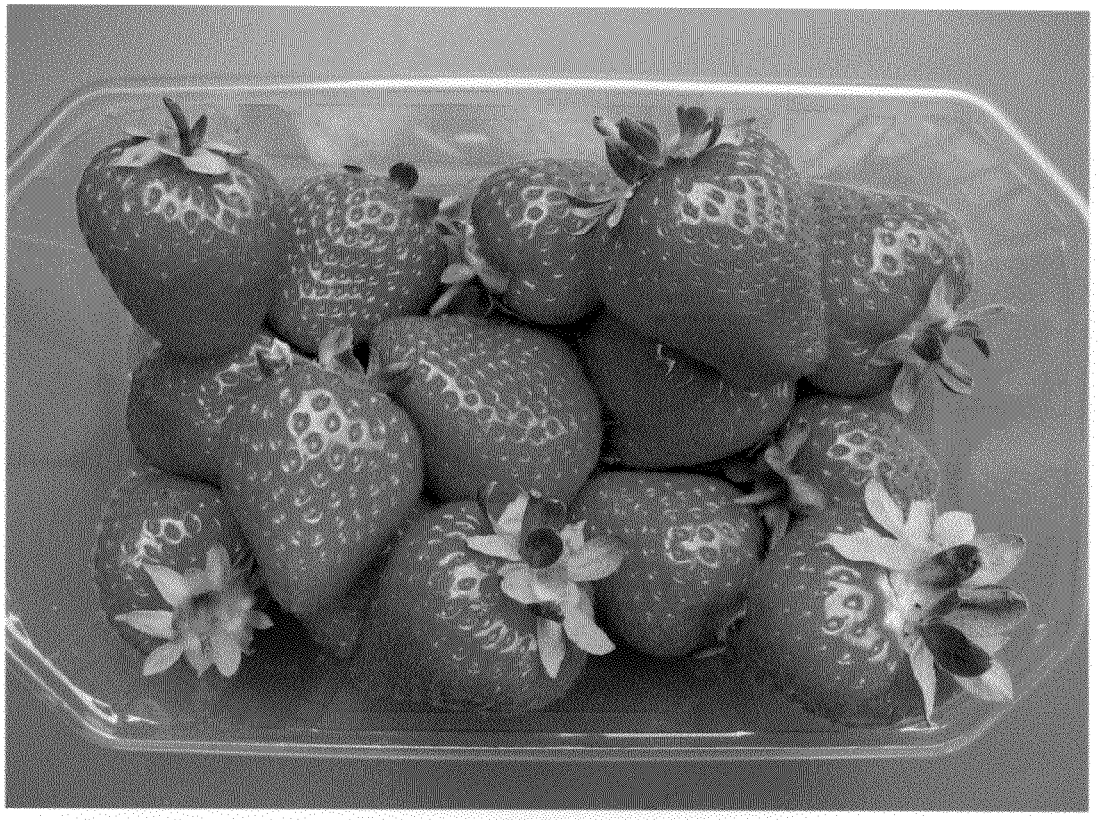
FIG. 1 shows a close-up of whole fruit.
Figure 2:
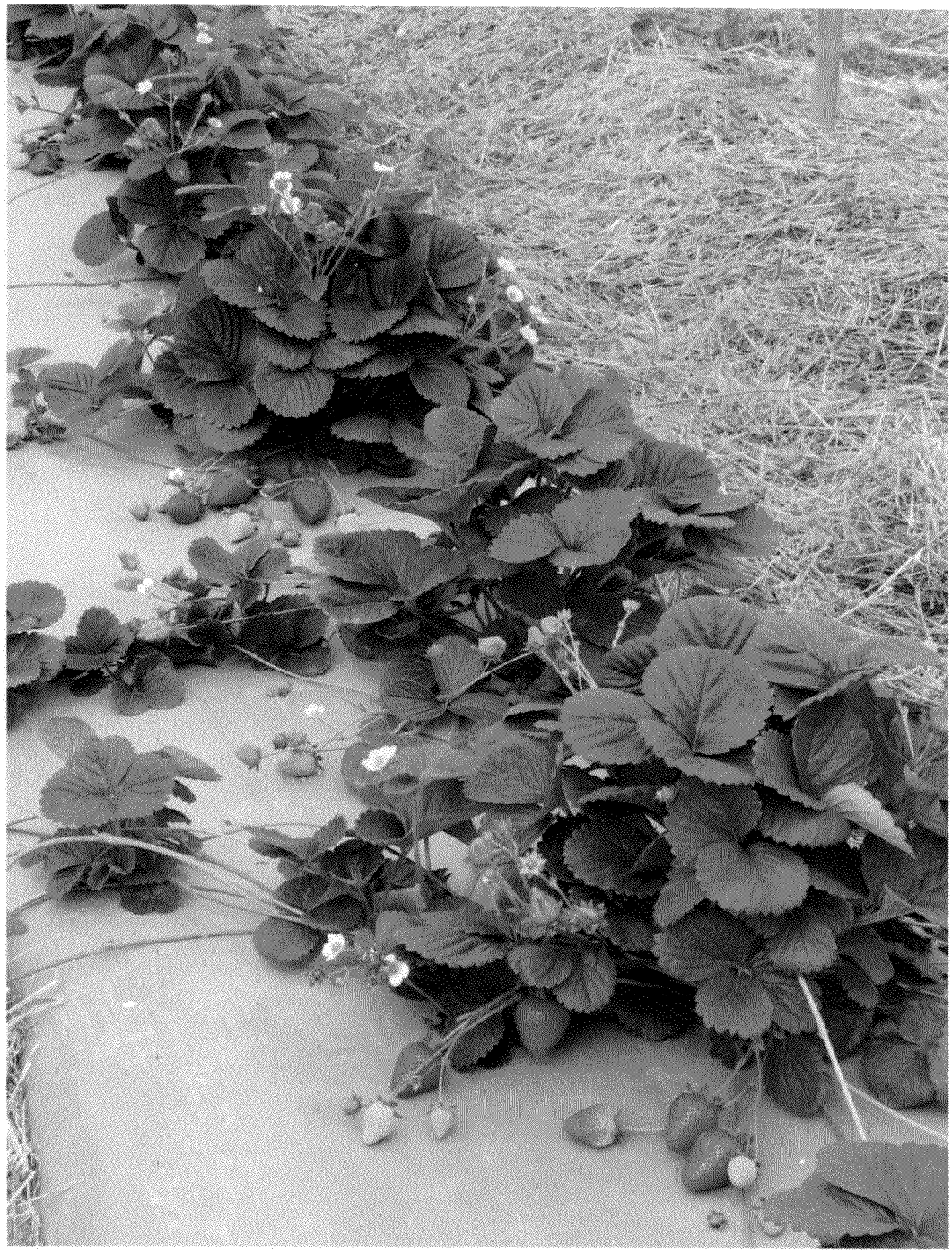
FIG. 2 shows overall plant habit of numerous plants.
Figure 3:
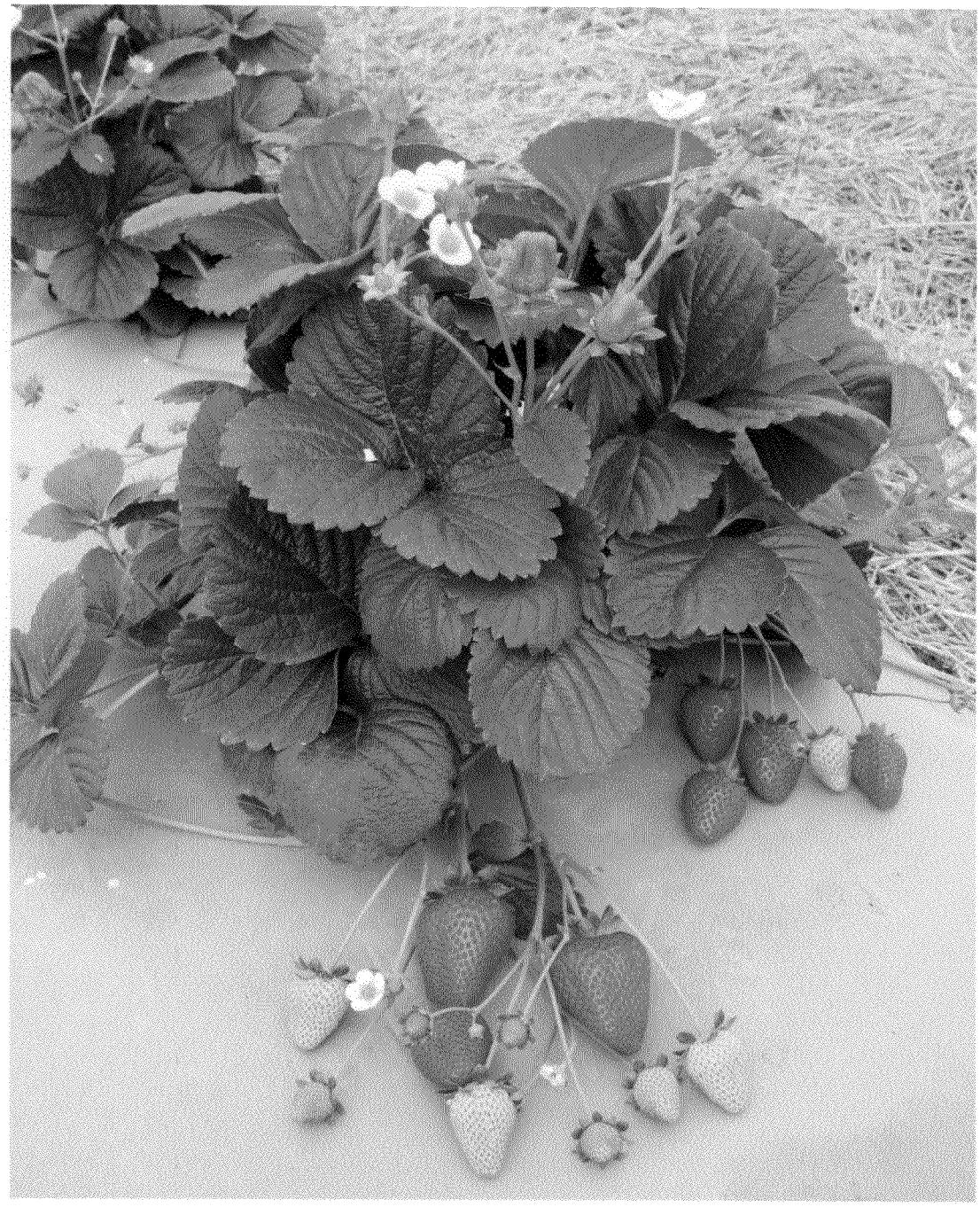
FIG. 3 shows a close-up of overall plant habit including fruit at various stages of development.

The following detailed descriptions set forth the distinctive characteristics of 'Buddy'. The data which define these characteristics is based on observations taken in East Malling, Kent, United Kingdom on Jul. 12, 2012. This description is in accordance with UPOV terminology. Color designations, color descriptions, and other phenotypical descriptions may deviate from the stated values and descriptions depending upon variation in environmental, seasonal, climatic, and cultural conditions. 'Buddy' has not been observed under all possible environmental conditions. The botanical description of 'Buddy' was taken from 3 month-old plants. Color references are primarily to The R.H.S. Colour Chart of The Royal Horticultural Society of London $5^{th}$ Edition. Descriptive terminology follows the *Plant Identification Terminology, An Illustrated Glossary,* $2^{nd}$ edition by James G. Harris and Melinda Woolf Harris, unless where otherwise defined.

DETAILED BOTANICAL DESCRIPTION OF THE PLANT

Classification:
- *Family.*—Rosaceae.
- *Species.*—*Fragaria×ananassa.*
- *Common name.*—Strawberry.
- *Denomination.*—'Buddy'.

Parentage:
- *Female parent.*—'Diamante' (U.S. Plant Pat. No. 10,435).
- *Male parent.*—'DNBL205' (unpatented).

Plant:
- *Growth habit.*—Semi-erect.
- *Height.*—22.8 cm.
- *Diameter.*—25.6 cm.
- *Number of crowns/plant.*—3.
- *Vigor.*—Medium.

Terminal leaflets:
- *Size.*—Length: 10.7 cm. Width: 10.5 cm. Length/width ratio: 1.02.
- *Number of teeth/terminal leaflet.*—16.
- *Shape of teeth.*—Serrate to crenate.
- *Color.*—Upper surface: RHS N137B. Lower surface: RHS N138B.
- *Shape in cross section.*—Concave.
- *Blistering.*—Medium.
- *Glossiness.*—Non-glossy.
- *Number of leaflets.*—3.
- *Base shape.*—Obtuse to rounded.
- *Apex descriptor.*—Obtuse to rounded.
- *Pubescence density.*—Light to moderate. Color: RHS NN155B.
- *Margin.*—Serrate to crenate.
- *Texture.*—Course; heavily veined.
- *Venation pattern.*—Pinnate. Color: Upper surface: RHS 144B. Lower surface: RHS 145B.

Petiole:
- *Length.*—15.0 cm.
- *Diameter.*—0.5 cm.
- *Color.*—RHS 145A.
- *Pubescence density.*—Dense. Color: RHS NN155B.
- *Anthocyanin.*—Absent.
- *Pose of hairs.*—Perpendicular.
- *Texture.*—Rough.

Petiolule:
- *Length.*—0.9 cm.
- *Diameter.*—0.23 cm.
- *Color.*—RHS 145A.

Stipule:
- *Length.*—19.6 mm.
- *Width.*—1.03 mm.
- *Texture.*—Smooth.
- *Color.*—RHS 145A.
- *Anthocyanin.*—Weak.

Stolon:
- *Number of daughter plants.*—25.
- *Anthocyanin.*—Absent.
- *Thickness.*—0.38 cm.
- *Pubescence.*—Moderate to dense.

Inflorescence:
- *Position relative to foliage.*—Vertical and above foliage.
- *Time of flowering* (50% *of plants at first flower*).—Various (everbearing).
- *Corolla.*—Form: Petals overlapping. Length: 2.8 cm. Width: 2.6 cm. Depth: 1.5 cm.
- *Petals.*—Shape: Globose oblate. Apex: Truncate to slightly obtuse. Base: Attenuate. Margin: Entire. Spacing: Overlapping. Length: 1.1 cm. Width: 1.1 cm. Length/width ratio: 1.0. Color (both upper and lower surfaces): RHS 155C. Texture: Medium.
- *Calyx.*—Diameter: 3.3 cm. Diameter of calyx relative to corolla on secondary flowers: Same size. Inner calyx diameter relative to outer on secondary flowers: Same size.
- *Sepal.*—Margin: Entire. Length: 1.03 cm. Width: 0.46 cm. Typical and observed sepal number per flower: 12.3. Color: RHS 144A. Anthocyanin: Absent. Texture: Smooth.
- *Peduncle.*—Length: 15.6 cm. Diameter: 0.4 cm. Color: RHS N144B. Pubescence: Dense.

Reproductive organs:
- *Stamens.*—Number: 28. Color: RHS 1C. Filament: Length: 0.2 cm. Diameter: 0.06 cm. Anthers: Color: RHS 13A. Length: 1.1 cm. Diameter: 0.073 cm. Pollen amount: Moderate. Color: RHS 13A.
- *Pistils.*—Style: Length (including stigma): 1.1 mm. Diameter (including stigma): 0.1 mm. Color: RHS 12B. Stigma: Color: RHS 12B.
- *Receptical color.*—RHS N144B.

Fruiting truss:
- *Length.*—21.2 cm.
- *Attitude at first picking.*—100 degrees.

Fruit:
- *Size.*—Large.
- *Length.*—4.17 cm.
- *Width.*—3.13 cm.
- *Length/width ratio.*—1.3 (Longer than broad).
- *Fruit hollow center* (*cavity*).—Slight.
- *Weight* (*per individual berry*).—22.8 g.
- *Predominant fruit shape.*—Cordate.
- *Difference in shape between primary and secondary fruits.*—First fruit is ridged and slightly wedged; second fruit is cordate.
- *Fruit skin color.*—RHS 44A.
- *Evenness of fruit color.*—Even or very slightly uneven.
- *Fruit glossiness.*—Glossy.
- *Attitude of calyx segments.*—Outwards.
- *Achenes.*—Insertion of achenes: Below surface. Color: RHS 1A. Width of band without achenes: Absent or very narrow.
- *Firmness of flesh* (*when fully ripe*).—Medium.
- *Firmness of skin.*—Firm.
- *Internal color.*—RHS 35A.
- *Color of core.*—RHS 36A.
- *Sweetness.*—Average Brix is 7.5.
- *Acidity.*—Low to medium.
- *Type of bearing.*—Everbearing.
- *Grams of fruit/plant.*—843.9 g.
- *Time of ripening* (50% *of plants with first ripe fruit*).—Everbearing so time of fruit ripening varies.
- *Yield.*—Medium.

Disease and pest resistance:
- *Phytophthora cactorum.*—Moderately resistant.
- *Verticillium dahliae.*—Moderately resistant.
- *Podosphaera aphanis.*—Susceptible.

COMPARISON WITH PARENTAL AND COMMERCIAL VARIETIES

When 'Buddy' is compared to the female parent 'Diamante' (U.S. Plant Pat. No. 10,435), 'Buddy' has cordate shaped berries, whereas 'Diamante' has long, rounded, conic shaped berries. In addition, 'Buddy' has darker skin color and a higher level of soluble solids (Brix) than 'Diamante'.

When 'Buddy' is compared to the commercial variety 'Portola' (U.S. Plant Pat. No. 20,552), 'Buddy' has smaller secondary and tertiary berries, berries with firmer texture and sweeter flavor and approximately 30% lower yield than 'Portola'. Additionally, 'Buddy' has cordate shaped berries, whereas 'Portola' has symmetrical conic shaped berries

We claim:

1. A new and distinct variety of strawberry plant named 'Buddy' as described and shown herein.

* * * * *